(12) United States Patent
Petit et al.

(10) Patent No.: US 6,485,908 B1
(45) Date of Patent: *Nov. 26, 2002

(54) MUTATION WITHIN THE CONNEXIN 26 GENE RESPONSIBLE FOR PRELINGUAL NON-SYNDROMIC DEAFNESS AND METHOD OF DETECTION

(75) Inventors: Christine Petit, le Plessis-Robinson (FR); Françoise Denoyelle-Gryson, Sceaux (FR); Dominique Weil, Paris (FR); Sandrine Marlin-Duvernois, Colombes (FR); Jean-Luc Guesdon, Sevres (FR)

(73) Assignee: Institut Pasteur, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/485,415

(22) PCT Filed: Aug. 14, 1998

(86) PCT No.: PCT/EP98/05175

§ 371 (c)(1),
(2), (4) Date: May 3, 2000

(87) PCT Pub. No.: WO99/09210

PCT Pub. Date: Feb. 25, 1999

Related U.S. Application Data

(60) Provisional application No. 60/055,863, filed on Aug. 15, 1997.

(51) Int. Cl.[7] .......................... C12Q 1/68; C12P 19/34; C07H 21/04
(52) U.S. Cl. ................ 435/6; 435/91.1; 435/91.2; 536/23.1; 536/24.3
(58) Field of Search .................... 435/6, 91.2, 91.1; 536/23.1, 24.3

(56) References Cited

U.S. PATENT DOCUMENTS 5,998,147 A    12/1999   Petit et al. ..................... 435/6

OTHER PUBLICATIONS

Sambrook et al., Hybridization of Radiolabeled Oligonucleotides to Genomic DNA, Molecular Cloning—A Laboratory Manual, 9.56–9.57 (1989).
Marazita et al., Genetic Epidemiological Studies of Early-–Onset Deafness in the U.S. School–Age Population, American Journal of Medical Genetics 486–491 (1993).
Morton, N.E., Genetic Epidemiological of Hearing Impairment, Annals of the New York Academy of Sciences, vol. 630, 16–31 (1991).
Kiang et al., Upstream genomic sequence of the human connexin26 gene, GENE, 165–171 (1997).
Petit, C., Autosomal recessive non–syndromal hearing loss, Genetics and Hearing Impairment, Chap. 21, 197–211 (1996).
Petit, C., Genes responsible for human hereditary deafness: symphony of a thousand, Nature Genetics, vol. 14, 385–391 (1996).
Verhoeven et al., A Gene for Autosomal Dominant Nonsyndromic Hearing Loss (DFNA12) Maps to Chromosome 11q22–24, Am. J. Hum. Genet., 1168–1173 (1997).
Campbell et al., A new locus for non–syndromal, autosomal recessive, sensorineural hearing loss (DFNB16) maps to human chromosome 15q21–q22, J. Med. Genet., 1015–1017 (1997).
Guilford et al., A non–syndromic form of neurosensory, recessive deafness maps to the pericentromeric region of chromosome 13q, Nature Genetics, vol. 6, 24–28 (1994).
Maw et al., The Contribution of the DFNBI Locus to Neurosensory Deafness in a Caucasian Population, Am. J. Hum. Genet., 629–635 (1995).
Gasparini et al., Linkage of DFNB1 to Non–Syndromic Neurosensory Autosomal–Recessive Deafness in Mediterranean Families, Eur. J. Hum. Genet. 83–88 (1997).
Kelsell et al., Connexin 26 mutations in hereditary non–syndromic sensorineural deafness, Nature, vol. 387, 80–83 (1997).
Smith et al., Fluorescence detection in automated DNA sequence analysis, Nature, vol. 321, 674–679 (1986).
Liu et al., Mutations in the myosin VIIA gene cause non-–syndromic recessive deafness, Nature Genetics, vol. 16, 188–190 (1997).
Weil et al., The autosomal recessive isolated deafness, DFNB2, and the Usher 1B syndrome are allelic defects of the myosin–VIIA gene, Nature Genetics, vol. 16, 191–193 (1997).
Beaudet et al., A Suggested Nomenclature for Designating Mutations, Human Mutation, 245–248 (1993).
Chevrier et al., PCR product quantification by non–radioactive hybridization procedures using an oligonucleotide covalently bound to microwells, Molecular and Cellular Probes, vol. 7, No. 3, 187–197 (1993).
Chevrier et al., Rapid detection of Salmonella subspecies I by PCR combined with non–radioactive hybridization using covalently immobilized oligonucleotide on a microplate, FEMS—Immunology and Medical Microbiology, vol. 10, 245–252 (1995).
Riesner et al., Temperature–gradient gel electrophoresis of nucleic acids: Analysis of conformational transitions, sequence variations, and protein–nucleic acid interactions, Electrophoresis, vol. 10, 377–389 (1989).

(List continued on next page.)

Primary Examiner—W. Gary Jones
Assistant Examiner—Jehanne Souaya
(74) Attorney, Agent, or Firm—Finnegan, Henderson, Farabow, Garrett & Dunner, LLP

(57) ABSTRACT

A purified polynucleotide having a chain of nucleotides corresponding to a mutated sequence, which in wild-type form encodes a polypeptide implicated in hereditary sensory defect, wherein the mutated purified polynucleotide presents a mutation responsible for prelingual non-syndromic deafness selected from the group consisting of a specific deletion of at least one nucleotide.

12 Claims, 1 Drawing Sheet

OTHER PUBLICATIONS

Lessa et al., Screening techniques for detecting allelic variation in DNA sequences, Molecular Ecology, vol. 2, 119–129 (1993).

Lee et al., Transcriptional Downregulation of Gap–junction Proteins Blocks Junctional Communication in Human Mammary Tumor Cell Lines, The Journal of Cell Biology, vol. 118, No. 5, 1213–1221 (1992).

Borresen–Dale et al., Temporal Temperature Gradient Gel Electrophoresis on the DCode™ System—A Comparison to DGGE and CDGE in Mutation Screening, Bio–Rad, Us/EG Bulletin 2133.

Pennisi, "The Architecture of Hearing," Science, vol. 278, pp. 1223–1224 (1997).

Lynch, et al., Nonsyndromic Deafness DFNA1 Associated with Mutation of a Human Homolog of the *Drosophila* Gene *Diaphanous*, Science, vol. 278, pp. 1315–1318 (1997).

MUTATION WITHIN THE CONNEXIN 26 GENE RESPONSIBLE FOR PRELINGUAL NON-SYNDROMIC DEAFNESS AND METHOD OF DETECTION

This application is an application filed under 35 U.S.C. §371 based on PCT/EP98/05175, filed Aug. 14, 1998, which claims priority to U.S. Provisional Application No. 60/055,863, filed Aug. 15, 1997.

BACKGROUND OF THE INVENTION

The present invention concerns a mutation responsible for autosomal prelingual non-syndromic deafness and a method for the detection of this hereditary sensory defect for homozygous and heterozygous individuals. The invention concerns more particularly a specific deletion of at least one nucleotide in the connexin 26 (Cx 26) gene and especially in a guanosine rich region, notably between the nucleotides 27 and 32. The invention is also directed to the use of polynucleotide, or fragments thereof, for example as tools useful for the in vitro detection of a mutation of a gene belonging to the Cx26 gene family.

Profound or severe prelingual deafness affects one child in a thousand in developed countries (Morton N E. Genetic epidemiology of hearing impairment. In *Genetics of hearing impairment*. (The New York Acad Sci, New York 1991; 630:16–31). It is a major handicap as it impedes language acquisition.

According to studies performed in a U.S. population of children with non-syndromic (isolated) prelingual deafness and in whom an obvious environmental cause has been excluded, it is estimated that up to two-thirds of the cases have a genetic basis (Marazita M L, Ploughman L M, Rawlings B, Remington E, Arnos K S, Nance W E. Genetic epidemiological studies of early-onset deafness in the U.S. school-age population. *Am J Med Genet* 1993; 46:486–91). These forms are mainly sensorineural and are almost exclusively monogenic. The major mode of inheritance is autosomal recessive (DFMB), involving 72% to 85% of cases, this fraction increasing to 90% when only profound deafness is taken into account.

Autosomal recessive prelingual deafness is known to be genetically highly heterogeneous. Estimates of the number of DFNB loci vary from thirty to one hundred (Petit C. Autosomal recessive non-syndromal hearing loss. In *Genetics and Hearing Impairment*. Martini A, Read A P, Stephens D, eds (Whurr, London) 1996; 197–212), for a review), of which fourteen have so far been mapped to the human chromosomes (Petit C. Genes responsible for human hereditary deafness: symphony of a thousand. *Nature Genet* 1996; 14:385–91) for review, (verhoeven K, Van Camp G, Govaerts P J, et al. A gene for autosomal dominant non-syndromic hearing loss (DFNA12) maps to chromosome 11q22–24. *Am J Hum Genet* 1997; 60:1168–74 and Campbell D A, McHale D P, Brown K A, et al. A new locus for non-syndromal autosomal recessive sensorineural hearing loss (DFNB16) maps to human chromosome 15q21–q22. *J Med Genet* 1997; in press).

A majority of the families attending genetic counseling clinics consist of normal hearing parents with a single deaf child who wish to know the risk of recurrence of the defect. In most cases, given the major role of environmental causes of prelingual deafness, it is not usually possible even to recognize whether the hearing loss is of genetic origin. Genetic counseling in such families would be greatly improved by an ability to detect DFNB mutations. In this respect, the high genetic heterogeneity of the condition represents a major obstacle.

After the initial identification of the DFNB1 locus on 13q11 in a large consanguineous Tunisian family (Guilford P, Ben Arab S, Blanchard S, et al. A non-syndromic form of neurosensory, recessive deafness maps to the pericentromeric region of chromosome 13q. *Nature Genet* 1994; 6:24–8), two studies performed on New Zealand/Australian families (Maw MA, Allen-Powell D R, Goodey R J, et al. The contribution of the DFNB1 locus to neurosensory deafness in a Caucasian population. *Am J Hum Genet* 1995; 57:629–35), and on Italian/Spanish families (Gasparini P, Estivill X, Volpini V, et al. Linkage of DFNB1 to non-syndromic neurosensory autosomal-recessive deafness in Mediterranean families. *Eur J Hum Genet* 1997; 5:83–8) suggested that this locus might be a major contributor to prelingual deafness in these populations, although individual lod scores obtained in these families were not significant owing to the small size of these families.

Recently, the Cx26 gene, which: encodes a gap junction protein, connexin 26, has been shown to underlie DFNB1 deafness. Two different C->A substitutions resulting in premature stop codons in three DFNB1 linked consanguineous Pakistani families have been reported (Kelsell D P, Dunlop J, Stevens H P, et al. Connexin 26 mutations in hereditary non-syndromic sensorineural deafness. *Nature* 1997; 387:80–3). These two substitutions were identified, respectively, at codon 77 and at codon 24. This result has offered the opportunity directly to assess this hypothesis.

The difficulties encountered in genetic counseling for prelingual non-syndromic deafness due to the inability to distinguish genetic and non-genetic deafness in the families presenting a single deaf child was one of the reasons that led the inventors to undertake a characterization of the spectrum and prevalence of mutations present in the Cx26 gene in 35 families from several parts of the world with autosomal recessive prelingual deafness.

SUMMARY OF THE INVENTION

The determination of a mutation in the Cx26 gene has notably rendered possible the use of a detection probe as a tool for the identification of a specific form of autosomal prelingual non-syndromic deafness, and more particularly the useful role of a newly identified 30delG (a G deletion at position 30; position 1 being the first base of the initiator. codon) mutation in such families. This invention establishes that the contribution of the DFNB1 locus predominantly results essentially from the 30delG mutation. It is now believed that the 30delG accounts for about three-quarters of all recessive DFNB1 mutations.

The invention is thus intended to provide a purified polynucleotide having a chain of nucleotides corresponding to a mutated sequence, which in a wild form encodes a polypeptide implicated in hereditary sensory defect. The mutated purified polynucleotide presents a mutation responsible for prelingual non-syndromic deafness.

The invention also provides oligonucleotides comprising of 15 to 50 consecutive nucleotides of the mutated purified polynucleotide that are useful as primers or as probes.

In addition, the invention aims to supply a method and a kit for the detection of the hereditary sensory defect for homozygous as heterozygous individuals.

According to the invention, the purified polynucleotide having a chain of nucleotides corresponding to a mutated sequence, which encodes in a wild form a polypeptide implicated in hereditary sensory defect, presents a mutation responsible for prelingual non-syndromic deafness selected from the group consisting of a specific deletion of at least one nucleotide.

By mutation, according to the invention it means a specific deletion of at least one nucleotide. Thus, a mutated sequence means a polynucleotide sequence comprising at least a mutation.

A chain of nucleotides, according to the invention, means a polynucleotide, which encodes not necessarily a polypeptide, but which presents between 27 and 2311 nucleotides linked together.

The invention particularly concerns a purified polynucleotide wherein, the specific mutation is a deletion located in a region encoding connexin 26 of chromosome 13q11–12, preferably located in a guanosine rich region starting at nucleotide 27 preferably at nucleotide 30, and extending to nucleotide 32 or nucleotide 35, all the recited nucleotides being inclusive. More particularly according to the invention, the specific deleted purified polynucleotide encodes for a truncated polypeptide.

By truncated polypeptide, according to the invention it means a fragment of the polypeptide, which does not present the properties of the wild form of the polypeptide either in length, in amino acid composition, or in functional properties.

A preferred embodiment of a specific deletion is a guanosine deletion at position 30, also called "30delG mutation". Another preferred embodiment of the specific deletion is a 38 bp deletion beginning at position 30.

The invention also includes a purified polynucleotide, which hybridizes specifically with any one of the polynucleotides as defined above under the following stringent conditions: at low temperatures between 23° C. and 37° C., in the presence of 4×SSC buffer, 5×Denhardt's solution, 0.05% SDS, and 100 µg/ml of salmon sperm DNA. (1×SSC corresponds to 0.15 M NaCl and 0.05M sodium citrate; 1×Denhardt's solution corresponds to 0.02% Ficoll, 0.02% polyvirylpyrrolidone and 0.02% bovine serum albumin)

The invention also concerns an oligonucleotide useful as a primer or as a probe comprising 15 to 50 consecutive nucleotides of the polynucleotide according to any one of the polynucleotides as defined above. The oligonucleotide sequence is selected from the following group:

A first couple:
5'-TCTTTTCCAGAGCAAACCGCC(SEQ ID No. 1)-3'
5'-TGAGCACGGGTTGCCTCATC(SEQ ID No. 2)-3'.

The length of the PCR product has been obtained from 285 bp in length;

A second couple allowing to explore the other part of the reading frame:
5'-GACACGAAGATCAGCTGCAG(SEQ ID No. 3)-3'
5'-CCAGGCTGCAAGAACGTGTG(SEQ ID No. 4)-3'

A third couple:
5'-CTAGTGATTCCTGTGTTGTGTGC(SEQ ID No. 9)-3'; and
5' ATAATGCGAAAAATGAAGAGGA(SEQ :ID No. 10)-3' and A fourth couple:
5'-CGCCCGCCGCGCCCCGCGCCCGGCCCGCCG CCCCCGCCCCCTAGTGATTCCT GTGTTGTGTGC (SEQ ID No. 14)-3'; and
5' ATAATGCGAAAAATGAAGAGGA(SEQ ID No. 10)-3'.

Another oligonucleotide useful as a probe is selected from the following group:
5'-AGACGATCCTGGGGGTGTGAACAAA(SEQ ID No. 5)-3'
5'-ATCCTGGGGGTGTGA(SEQ ID No. 6)-3'
5'-AGACGATCCTGGGGGCTCACCGTCCTC(SEQ ID No. 7)-3'.

In addition, the invention concerns a method for the detection of an hereditary sensory: defect, namely autosomal prelingual non-syndromic deafness, for homozygous as heterozygous individuals in a biological sample containing DNA, comprising the steps of:
  a) bringing the biological sample into contact with a oligonucleotide primers as defined above, the DNA contained in the sample having been optionally made available to hybridization and under conditions permitting a hybridization of the primers with the DNA contained in the biological sample;
  b) amplifying the DNA;
  c) revealing the amplification products;
  d) detecting the mutation.

Step d) of the above-described method may comprise a Single-Strand Conformation Polymorphism (SSCP), a Denaturing Gradient Gel Electrophoresis (DGGE) sequencing (Smith, L. M., Sanders, J. Z., Kaiser, R. J., Fluorescence detection in automated DNA sequence analysis. Nature 1986; 321:674–9); a molecular hybridization capture probe or a temperature gradient gel electrophoresis (TGGE).

Step c) of the above-described method may comprise the detection of the amplified products with an oligonucleotide probe as defined above.

According to the invention, a biological sample can be a blood sample extracted from people suffering from any kind of deafness with any criteria as follows: neurosensorial or mixed isolated deafness, advanced or not, at any degree of severity, concerning familial or sporadic case, or individuals exposed to noise, or individuals suffering from a low acoustic, or individuals susceptible to carry an anomaly in the gene, or from an embryo for antenatal diagnostic.

Another aim of the invention comprises a method for the detection of an hereditary sensory defect, the autosomal prelingual non-syndromic deafness, for homozygous and heterozygous individuals in a biological sample containing DNA, comprising the steps of:
  a) bringing the biological sample into contact with an oligonucleotide probe according to the invention, the DNA contained in the sample having been optionally made available to hybridization and under conditions permitting a hybridization of the primers with the DNA contained in the biological sample; and
  b) detecting the hybrid formed between the oligonucleotide probe and the DNA contained in the biological sample.

Step b) of the above-described method may consist in a single-strand conformation. Polymorphism (SSCP), a denaturing gradient gel electrophoresis (DGGE) or amplification and sequencing.

The invention also includes a kit for the detection of an hereditary sensory defect, the autosomal prelingual non-syndromic deafness, for homozygous as heterozygous individuals, said kit comprising:
  a) oligonucleotides according to the invention;
  b) the reagents necessary for carrying out DNA amplification; and
  c) a component that makes it possible to determine the length of the amplified fragments or to detect a mutation.

BRIEF DESCRIPTION OF THE DRAWINGS

This invention will be more described in greater detail by reference to the drawings in which:

FIG. 1 depicts the results of temperature gradient gel electrophoresis for detection of mutants in which:

Figure 1:
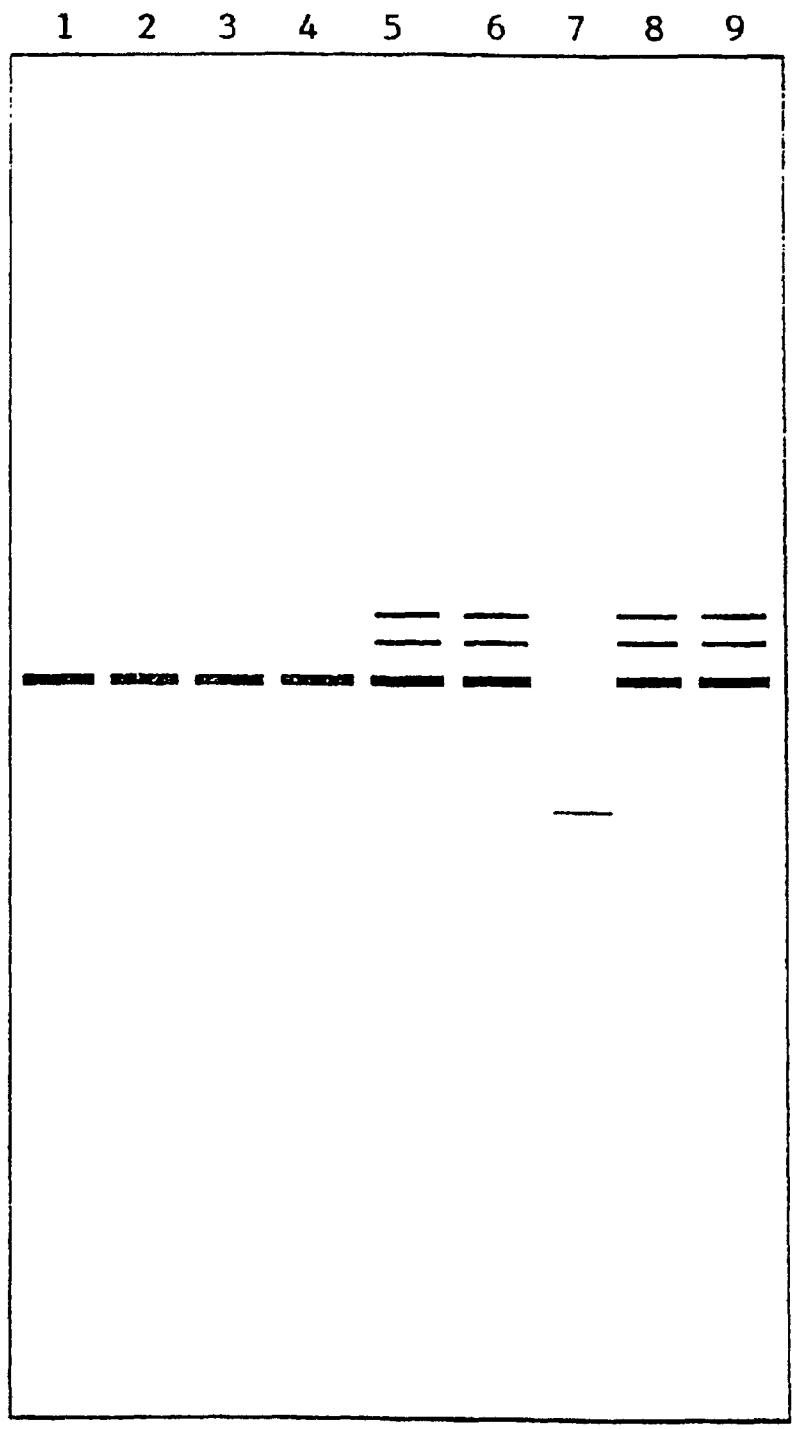

Lanes 1 and 2: DNA from normal patients.

Lanes 3 and 4: DNA from homozygous patients with 30delG mutation.

Lanes 5 and 6: DNA from heterozygous patients.

Lane 7: PCR control without DNA.

Lane 8: PCR fragment amplified from a normal DNA and hybridized with a standard DNA fragment harboring the 30delG mutation.

Lane 9: PCR fragment amplified from a mutant homozygous DNA and hybridized with a normal standard DNA fragment harboring the guanine 30.

DETAILED DESCRIPTION OF THE INVENTION

Prelingual non-syndromic (isolated) deafness is the most frequent hereditary sensory defect in children. The inheritance in most is autosomal recessive. Several dozens of genes might be involved, only two of which, DFNB1 and DFNB2, have so far been identified (Kelsell, D. P., et al., Connexin 26 mutations in hereditary non-syndromic sensorineural deafness. *Nature* 1997; 387:80–3; Liu, X–Z, et al., Mutations in the myosin VIIA gene cause non-syndromic recessive deafness, *Nature Genet* 1997; 16:188–90; and Weil, D., et al., The autosomal recessive isolated deafness, DFNB2, and the Usher 1B syndrome are allelic defects of the myosin-VIIA. *Nature Genet* 1997; 16:191–3). A search was made searched for mutations in the gene encoding connexin 26, Cx26, which has recently been shown to be responsible for DFNB1. Mutation analysis of Cx26 was performed by PCR amplification on genomic DNA and sequencing of the single coding exon.

EXAMPLE 1

Patients

Thirty-five affected families from various geographical regions, mainly France, New Zealand and Australia, Tunisia and Lebanon, were studied. They could be classified into three categories: (1) consanguineous families each having a significant linkage to the DFNB1 locus; (2) small non-consanguineous families in which linkage analysis was compatible with the involvement of DFNB1; and (3) small families in which no linkage analysis had been undertaken.

The first category consists of six large families living in geographically isolated regions. Five were from Tunisia, two from the north and three from the south. Linkage to the DFNB1 locus in the two families from northern Tunisia (families 20 and 60) had previously been reported (Guilford P, Ben Arab S, Blanchard S, et al., A non-syndromic form of neurosensory, recessive deafness maps to the pericentromeric region of chromosome 13q. *Nature Genet* 1994; 6:24–8); the three families from southern Tunisia (S15, S19 and ST) and the family from Lebanon (LH) comprise total of three, five, two, and five deaf children, respectively, the deafness being of severe or profound degree. The marriages were between first cousins (S15, ST and LH) and between first and second cousins (S19). Linkage analysis of these six families resulted in individual lod scores ranging from 2.5 to 10 with polymorphic markers from the DFNB1 region (D13S175, D13S141, D13S143 and D13S115).

The second category of patients comprises seven New Zealand families with at least two deaf siblings (families 51, 1160, 1548, 1608, 1773, 1873, 1877) and one Australian (9670) family. Family 1608 was atypical in that four siblings sharing the same DFNB1 marker haplotypes had a mild to moderate deafness (severe at high frequency), with the child of one of them being profoundly deaf. In family 1873, the unrelated parents (individuals II.2 and II.3) were deaf as well as their two children, and we have therefore considered this as two families, bringing to nine the total of independent families. Apart from families 1608 and 1873, no parent acknowledged any hearing impairment. These nine families showed cosegregation between deafness and polymorphic markers of the DFNB1 region with maximum individual lod scores ranging from 0.6 to 1.2. Ten other families in the original study of Maw et al. (Maw M A, Allen-Powell D R, Goodey R J, et al. The contribution of the DFNB1 locus to neurosensory deafness in a Caucasian population. *Am J Hum Genet* 1995; 57:629–35) had shown no cosegregation and one other cosegregating family was not tested for Cx26 mutations. The New Zealand families were all of Caucasian origin with no known Polynesian admixture. According to the antecedent family names, the ancestral proportion among the families reflected that of the general Caucasian New Zealand population with the great predominance being of Anglo-Celtic patrimony and a small fraction due to migration from continental Europe. Neither parental consanguinity, nor links between any of the families were recognized. In the Australian case, the father was from Northern Ireland and the mother from Yorkshire, England.

The third category is composed of nineteen families living in France and two in New Zealand, each with at least two children having a severe to profound deafness. No parent acknowledged any hearing impairment, except for the mother in family P16 and the father in family P17 who had moderate and progressive high-frequency hearing loss. Five of these families had foreign ancestors. from Lebanon (family P3), Turkey (family P4), Portugal (family; P9), Algeria (family P14) and Poland (father in family P16). In two of the families (P7 and P14), the parents were distantly related.

EXAMPLE 2

Amplification of the coding exon of Cx26 PCRs were carried out on genomic DNA using a set of primers that allowed the amplification of the entire coding sequence of the Cx26 gene, which consists of a single coding exon (Kelsell DP, Dunlop J, Stevens H P, et al. Connexin 26 mutations in hereditary non-syndromic sensorineural deafness. *Nature* 1997; 387: 80–3). Primer sequences were as follows:

5'-TCTTTTCCAGAGCAAACCGCC(SEQ ID No. 1)-3' and
5'-TGAGCACGGGTTGCCTCATC(SEQ ID No. 2)-3'.

PCR conditions were: 35 cycles of 95° C., 1 min; 58° C., 1 min; 72° C., 2 min. The PCR product obtained was 777 bp in length.

EXAMPLE 3

DNA Sequencing

Sequencing of the PCR products was performed as previously described (Smith L M, Sanders J Z, Kaiser R J, et al., Fluorescence detection in automated DNA sequence analysis, *Nature* 1986; 321:674–9) using the dideoxy chain terminator method on an Applied Biosystems DNA sequencer ABI373 with fluorescent dideoxynucleotides. The primers used were the same as those for the PCR amplification plus two internal primers 5'-GACACGAAGATCAGCTGCAG(SEQ ID No. 3)-3' and
5'-CCAGGCTGCAAGAACGTGTG(SEQ ID No. 4)-3'.

EXAMPLE 4

Mutations in Consanguineous Tunisian and Lebanese DFNB1 Families

In these families the involvement of the DFNB1 locus could be demonstrated by linkage analysis. In four of the five families from Tunisia (S15, S19, 20, and 60) and in the Lebanese family (LH), the same mutation was detected in all affected children on both Cx26 alleles, namely, a deletion of a guanosine (G) in a sequence of six G extending from position 30 to 35 (position 1 being the first base of the initiator codon) (Table 1). This mutation is hereafter referred to as 30delG mutation according to the nomenclature proposed by Beaudet and Tsui ((Beaudet AL, Tsui L-C. A suggested nomenclature for designating mutations, *Hum Mutation* 1993; 2: 245–8)). It creates a frameshift, which results in a premature stop codon at nucleotide position 38. The mutation segregating in the fifth family from Tunisia (ST) was identified as a G to T transversion at nucleotide position G39 creating a premature stop codon (GAG->TAG) at codon 47, and was designated E47X. In each family, normal hearing parents were found to be heterozygous for the corresponding mutation.

EXAMPLE 5

Mutations in Small Nonconsanguineous New Zealand and Australian Families Consistent with DFNB1 Linkage In these families, segregation analysis has previously been reported as compatible with the involvement of the DFNB1 locus (Maw M A, Allen-Powell D R, Goodey R J, et al. The contribution of the DFNB1 locus to neurosensory deafness in a Caucasian population. *Am J Hum Genet* 1995; 57: 629–35). The deaf individuals from five of the nine families (51, 1160, 1608 (III.20), 1873 (II.3) and 1877) were homozygous for the 30delG mutation. The deaf children from family 1773 were heterozygous for 30delG. Deaf individual II.2 from family 1873 (see "subjects" and Table 1) was heterozygous for a deletion of 38 bp beginning at nucleotide position G30, designated 30del38. No other mutation was detected in the deaf children of family 1773 and the deaf individual (II.2) in family 1873. Nevertheless, in this last individual, a deletion of the polymorphic marker immediately proximal to the Cx26 gene (locus D13S175) had previously been observed (Maw M A, Allen-Powell D R, Goodey R J, et al. The contribution of the DFNB1 locus to neurosensory deafness in a Caucasian population. *Am J Hum Genet* 1995; 57: 629–35), which may indicate that a DNA rearrangement has impaired the functioning of the other Cx26 allele of the gene in cis. In family 9670, compound heterozygosity for a missense mutation (R184P) and an in frame single-codon deletion (delE138) was observed in affected siblings. In only one family (1548) was no Cx26 mutation detected. Results are summarized in Table 1.

EXAMPLE 6

Mutations in Small Families Uncharacterized for DFNB1 Linkage Living in France and New Zealand Nineteen families (P1 to 17, L14190 and L13131) living in France and two in New Zealand (families 1885 and 2254) were studied. In these families, cosegregation of the deafness with polymorphic markers had not been analysed. Deaf children from six of the twenty-one families (P1, P3, P5, P9, P10, and P16) were found to be homozygous for the mutation 30delG. In five additional families (P6, P11, P14, P17, and 1885), deaf children were heterozygous for this mutation; no other mutation was detected in these families. In the ten remaining families, no mutation in the Cx26 gene was found.

EXAMPLE 7

Molecular Hybridization Using Allele-specific Capture Probes

Molecular hybridization capture probe (see, e.g., D. Chevrier et al. PCR product quantification by non-radioactive hybridization procedures using an oligonucleotide covalently bound to microwells. Molecular and Cellular Probes 1993; 7: 187–197 and D Chevrier et al. Rapid detection of Salmonella subspecies I by PCR combined with non-radioactive hybridization using covalently immobilized oligonucleotide on a microplate. FEMS Immunology and Medical Microbiology 1995; 10: 245–252 each of which is incorporated by reference herein) permit specific detection of the 30delG mutation. The technique has been adapted to permit rapid diagnosis of prelingual non-syndromic deafness caused by the 30delG mutation. The technique provides certain advantages in a clinical setting because it uses stable, nonradioactive molecules, it can be easily automated, and it is well adapted to large scale analysis.

Using primers designed for PCR amplification, the region of interest in the Cx26 gene is amplified from genomic DNA samples. The primer sequences are as follows:
CONN3: 5'-CTAGTGATTCCTGTGTTGTGTGC(SEQ ID No. 9)-3'
CONN4: 5' ATAATGCGAAAAATGAAGAGGA(SEQ ID No. 10)-3'
PCR is performed with the CONN3 (SEQ ID No. 9) and CONN4 (SEQ ID No. 10) primers (1 $\mu$M each), an aliquot of the DNA to be analyzed (2 $\mu$l, 100–300 ng), 1.5 mM $MgCl_2$, 200 $\mu$M dNTP, and Taq polymerase. The amplification program consists of the following steps: 1) 95° C., 5 min; 2) addition of enzyme, 95° C., 1 min; 3) 60° C., 1 min (ramp rate=0.25° C./s); 4) 72° C., 1 min; 5) repeat steps 2 to 4 for 40 cycles; and 6) 72° C., 10 min. PCR products are verified by a rapid gel electrophoresis.

The amplified PCR product contains either the normal or the mutant Cx26 sequence. To distinguish between the normal and mutant sequence, two capture probes are designed. The sequences of these two capture probes are as follows:
For detection of normal sequence:
CONN6: 5'-AAAATCCTGGGGGGTGTG(SEQ ID No. 11)-3'
For detection of mutant sequence:
CONN7: 5'-AAAAAATCCTGGGGGTGTGA(SEQ ID No. 12)-3'
Each capture probe must be 22 nucleotides long. Furthermore, to be efficient, the capture probe must include an $A_7$ spacer at its 5' end and a hybridization region of 15 bases. Such a capture probe is able to specifically differentiate the mutant sequence from the normal sequence. Thus, CONN6 (SEQ ID No. 11) is designed to specifically hybridize with the normal sequence, whereas CONN7 (SEQ ID No. 12) is designed to specifically hybridize with the mutant sequence.

Before attaching the capture probes to a microtiter plate, they are phosphorylated at their 5' ends. The phosphorylation is carried out for 1 hour at 37° C. in presence of 20 nmoles of CONN6 (SEQ ID No. 11) or CONN7 (SEQ ID No. 12) oligonucleotides, 100 µM ATP, 10 units T4 polynucleotide kinase in 200 µl of buffer (50 mM Tris-HCl pH 7.4; 10 mM $MgCl_2$; 5 mM dithiothreitol; and 1 mM spermidine). The mixture is heated for 10 min. at 68° C. to inactivate the T4 polynucleotide kinase, then the oligonucleotide is precipitated by adding 145 µl of 10 M $CH_3COONH_4$, 15 µl $H_2O$, and 800 µl iced ethanol. After a 30 min. incubation in ice, the mixture is centrifuged for 20 min. at 12,000×g at 4° C. The resulting pellet is washed with 500 µl iced ethanol (70%) and dissolved in 800 µl of TE buffer. The phosphorylated oligonucleotide concentration is determined by optical density at 260 nm.

Before attaching the phosphorylated oligonucleotides to microplates, they are denatured by heating at 95° C. for 10 min. and rapidly cooled in ice to avoid the formation of secondary structure. 500 ng of phosphorylated CONN6 (SEQ ID No. 11) or CONN7 (SEQ ID No. 12) and 1 µl of 1 M 1-methylimidazole, pH 7, is added to each well of a microplate, which is kept on ice. The total volume of each well is adjusted to 70 µl with distilled water, before adding 30 µl of a cold, 1-ethyl-3(3-dimethylaminopropyl) carbodiimide solution (167 mM). The microplate is covered and incubated for 5 hours at 50° C. in an incubator (Thermomix® from Labsystems). After the 5-hour incubation, the microplate is washed three times with a warm solution (50° C.) of 0.4 N NaOH containing 0.25% SDS. The microplate is incubated for 5 min. with the same warm solution and washed again with warm NaOH/SDS (50° C.). Finally, the microplate is washed five times with TE buffer. The coated microplate can be kept several months at 4° C., if the wells are filled with TE buffer.

The amplified sequences from the genomic DNA samples are incubated with a biotinylated detection probe in the coated microplates. Unlike the capture probes, which are allele specific, the detection probe can hybridize with both the normal and mutant sequences. The sequence of the detection probe is:

CONN12: 5'-CAGCATTGGAAAGATCTGGCTCA(SEQ ID No. 13)-3'.

The amplified sequences and the detection probe, which is biotinylated at its 5' end, are denatured directly in the microplates by successively adding to each well: 95 µl of water, 5 µl of PCR reaction, 40 µl of biotinylated probe (SEQ ID No. 13) at 22 nM diluted in water,; and 14 µl 1 N NaOH. After 10 min., 21 µl of 1 M $NaH_2PO_4$ and 1% Sarkosyl is added to each well to bring the total volume to 175 µl per well. The final concentration of the detection probe is 5 nM. The microplate is covered and incubated overnight at 40° C. in an incubator (Thermomix® from Labsystems) and then extensively washed (5 times) with TBS-Tween to remove the excess biotinylated probe (SEQ ID No. 13).

An immunoenzymatic method is used to detect the hybridized probe. Each well receives 100 µl of the conjugate (Extravidine—alkaline phosphatase, Sigma E-2636) diluted 1/4000 in TBS-BSA-Tween. The microdlate is covered and incubated for 1 hour at 25° C. Following the incubation, the microplate is washed 5 times with TBS-Tween. Then 200 µl of preheated (37° C.) substrate (7.5 mg para-nitro-phenyl-phosphate in 20 ml of the following buffer: 1 M diethanolamine pH 9.8 containing 1 mM $MgCl_2$) are added to each well. The microplate is covered and incubated for 3 hours at 37° C. The absorbance is measured at 405 nm to determine the specific signal and at 630 nm to determine the background noise.

The hybridization ratio (R) between the signal obtained with CONN6 (SEQ ID No. 11) probe (normal sequence) and that obtained with CONN7 (SEQ ID No. 12) probe mutant sequence) is calculated. The calculated R values are used to determine the genotypes of the sample DNA as follows: homozygous for the normal Cx26 sequence ($R \geq 2$), heterozygous for the 30delG mutation ($0.5 < R < 2$), and homozygous for the 30delG mutation ($R \leq 0.5$). The range of the hybridization ratio (R) can be slightly modified when the number of samples increases. The following table represents an example of results obtained with 39 samples.

| Genotype: | Hybridization ratio (R) | | |
| --- | --- | --- | --- |
| | Normal | Homozygous 20delG | Heterozygous |
| | 5.96 | 0.48 | 1.33 |
| | 5.43 | 0.17 | 1.13 |
| | 3.39 | 0.21 | 0.73 |
| | 4.14 | 0.16 | 0.63 |
| | 4.09 | 0.28 | 1.4 |
| | 2.76 | 0.13 | 0.73 |
| | 2.2 | 0.21 | 0.76 |
| | 3.97 | 0.4 | 0.73 |
| | 4.07 | | 1.06 |
| | 3 | | |
| | 2.76 | | |
| | 3.66 | | |
| | 3.87 | | |
| | 3.92 | | |
| | 3.26 | | |
| | 5.17 | | |
| | 2.74 | | |
| | 4.51 | | |
| | 6.3 | | |
| | 3.49 | | |
| | 4.05 | | |
| | 3.17 | | |
| Number | 22 | 8 | 9 |
| Mean value | 3.91 | 0.26 | 0.94 |
| Standard deviation | 1.06 | 0.12 | 0.29 |
| Range | (6.3–2.2) | (0.48–0.13) | (1.4–0.63) |

EXAMPLE 8

Temperature Gradient Gel Electrophoresis

Temperature gradient gel electrophoresis (TGGE) permits the detection of any type of mutation, including deletions, insertions, and substitutions, which is within a desired region of a gene. (See, e.g. D. Reiner et al. Temperature-gradient gel electrophoresis of nucleic acids: Analysis of conformational transitions, sequence variations and protein-nucleic acid interactions. Electrophoresis 1989; 10: 377–389; E. P. Lessa and G. Applebaum Screening techniques for detecting allelic variation in DNA sequences. Molecular Ecology 1993; 2: 119–129 and A. L. B örresen-Dale et al. Temporal Temperature Gradient Gel Electrophoresis on the D code™ System. Bio-Rad US/EG Bulletin 2133; the entire disclosure of each publication is. incorporated by reference herein.) However, TGGE does not permit one to determine precisely the type of mutation and its location.

As in the previously described molecular hybridization technique, the region of interest in the Cx26 gene is first amplified from genomic DNA samples by PCR. The primer sequences are as follows:

CONN2:
5'-CGCCCGCCGCGCCCCGCGCCCGGCCCGCC GCCCCGCCCCCT AGTGATTCCTGTGTTGTGTGC (SEQ ID No. 14)-3'
CONN4: 5' ATAATGCGAAAAATGAAGAGGA(SEQ ID No. 10)-3'

PCR is performed with 1 μM of the CONN2 (SEQ ID No. 14) primer, which has a GC clamp at its 5' end, and 1 μM of the CONN4 (SEQ ID No. 10) primer, an aliquot of the DNA to be analyzed (2 μl, 100–300 ng), 1.5 mM MgCl$_2$, 200 μM dNTP, and Taq polymerase. The amplification program consists of the following steps: 1) 95° C., 5 min; 2) addition of enzyme, 95° C., 1 min; 3) 60° C., 1 min (ramp rate=0.25° C./s); 4) 72° C., 1 min; 5) repeat steps 2 to 4 for 40 cycles; and 6) 72° C., 10 min.

Analyzing these PCR amplification fragments by TGGE can differentiate between homozygous (normal or mutant) samples, which produce a single band on a gel, and heterozygous samples, which produce three bands. However, differentiating between genomic samples that are homozygous for the normal sequence and genomic samples that are homozygous for the 30delG mutants requires an additional step.

To differentiate normal homozygous versus mutant homozygous samples, an aliquot of the amplified PCR product is mixed with either a known, normal homozygous sample or a known, 30delG mutant homozygous sample and analyzed for heteroduplex formation. If the amplified PCR product derives from a normal, homozygous sample, it will form a heteroduplex with the known, 30delG mutant homozygous sample. On the other hand, if the amplified PCR product derives from a mutant, homozygous sample, it will form a heteroduplex with the known, normal homozygous sample. To promote heteroduplex formation in these mixtures, they are denatured at 95° C. for 5 min, followed by a renaturation step at 60° C. for 45 min.

The PCR fragments from the initial amplification and those that are subjected to the additional heating steps to permit heteroduplex formation are analyzed on a 10% polyacrylamide gel containing 7 M urea. By way of example, a 30 ml gel is prepared by combining the following ingredients:

12.6 g urea
0.75 ml 50×TAE
7.5 ml acrylamide:bisacrylamide (37.5:1) at 40%
water to bring volume to 30 ml
30 μl Temed (added extemporaneously)
300 μl 10% ammonium persulfate (added extemporaneously)

After adding the Temed and ammonium persulfate, the gel is poured between two glass plates (Dcode Universal Mutation Detection System® from BIORAD) and allowed to polymerize for 1 hour.

An aliquot (7.5 μl) of the PCR mixture is mixed with 7.5 μl of 2× sample solution (2 mM EDTA pH 8; 70% glycerol; 0.05% xylene cyanol; 0.05% bromophenol. blue), and introduced into a gel well. Electrophoresis is performed for 4–5 hours at 150V in 1.25×TAE buffer with a temperature gradient ranging from 61° C. to 62° C. at a rate of 0.2° C. per hour. Following electrophoresis, the gel is incubated for 6 min. in 1.25×TAE containing 25 μg/ml ethidium bromide. Excess ethidium bromide is removed by a 20 min. wash in 1.25×TAE, and the DNA fragments are visualized with a UV transilluminator.

A typical TGGE result is represented in FIG. 1. The amplified DNA from homozygous patients (normal or mutant) produces only one band. The amplified DNA from heterozygous patients results in three different fragments in the polyacrylamide gel. The more intense band, which migrates more rapidly, corresponds to both homoduplexes, which cannot be separated in this gel. The other two bands, which migrate more slowly, correspond to both kinds of heteroduplexes.

The DNA of normal homozygous patients can be differentiated from the DNA of mutant homozygous patients by analyzing the PCR fragments that were subjected to the conditions that permitted heteroduplex formation. Heteroduplexes form when the PCR amplified fragment from a normal homozygous genome is mixed with sequences from a known, mutant homozygous genome, or when the PCR amplified fragment from a mutant homozygous genome is mixed with sequences from a known, normal homozygous genome. These heteroduplexes are visible by TGGE analysis. Consequently, the DNA of normal and mutant homcygous patients can be easily differentiated by this technique using the primers described in the present study.

In all the known DFNB1 families (6/6), in all but one (8/9) of the putatively DFNB1-linked families, and in about half (11/21) of the families not tested for DFNB1 linkage, a mutation in Cx26 was detected. Furthermore, of the 44 chromosomes reckoned to be independent upon which a Cx26 mutant allele was identified or inferred, 33(75%) were found to carry the same deletion of a guanosine, G, at position 30 (30delG).

Cx26 mutations represent a major cause of recessively inherited prelingual deafness and would be implicated in about half of cases in the examined populations. In addition, one specific mutation, 30delG, accounts for the majority (about three-quarters in our series) of the Cx26 mutant alleles.

The wild type connexin 26 gene published in LEE S. W. et; al. (1992)J. Cell Biol. 118: 1213–1221 has the following. sequence:

1 GATTTAATCC TATGACAAAC TAAGTTGGTT CTGTCTTCAC CTGTTTTGGT
51 GAGGTLGTGT AAGAGTTGGT GTTTGCTCAG GAAGAGATTT AAGCATGCTT
101 GCTTACCCAG ACTCAGAGAA GTCTCCCTGT TCTGTCCTAG CTATGTTCCT
151 GTGTTGTGTG CATTCGTCTT TTCCAGAGCA AACCGCCCAG AGTAGAAGAT
201 GGATTGGGGC ACGCTGCAGA CGATCCTGGG GGGTGTGAAC AAACACTCCA
251 CCAGCATTGG AAAGATCTGG CTCACCGTCC TCTTCATTTT TCGCATTATG
301 ATCCTCGTTG TGGCTGCAAA GGAGGTGTGG GGAGATGAGC AGGCCGACTT
351 TGTCTGCAAC ACCCTGCAGC CAGGCTGCAA GAACGTGTGC TACGATCACT
401 ACTTCCCCAT CTCCCACATC CGGCTATGGG CCCTGCAGCT GATCTTCGTG
451 TCCAGCCCAG CGCTCCTAGT GGCCATGCAC GTGGCCTACC GGAGACATGA
501 GAAGAAGAGG AAGTTCATCA AGGGGGAGAT AAAGAGTGAA TTTAAGGACA
551 TCGAGGAGAT CAAAACCCAG AAGGTCCGCA TCGAAGGCTC CCTGTGGTGG
601 ACCTACACAA GCAGCATCTT CTTCCGGGTC ATCTTCGAAG CCGCCTTCAT
651 GTACGTCTTC TATGTCATGT ACGACGGCTT CTCCATGCAG CGGCTGGTGA
701 AGTGCAACGC CTGGCCTTGT CCCAACACTG TGGACTGCTT TGTGTCCCGG
751 CCCACGGAGA AGACTGTCTT TCACAGTGTT CATGATTGCA GTGTCTGGAA
801 TTTGCATCCT GCTGAATGTC ACTGAATTGT GTTATTTGCT AATTAGATAT
851 TGTTCTGGGA AGTCAAAAAA GCCAGTTTAA CGCATTGCCC AGTTGTTAGA
901 TTAAGAAATA GACAGCATGA GAGGGATGAG GCAACCCGTG CTCAGCTGTC

951 AAGGCTCAGT CGCCAGCATT TCCCAACACA
AAGATTCTGA CCTTAAATGC

1001 AACCATTTGA AACCCCTGTA GGCCTCAGGT
GAAACTCCAG ATGCCACAAT

1051 GAGCTCTGCT CCCCTAAAGC CTCAAAACAA
AGGCCTAATT CTATGCCTGT

1101 CTTAATTTTC TTTCACTTAA GTTAGTTCCA
CTGAGACCCC AGGCTGTTAG

1151 GGGTTATTGG TGTAAGGTAC TTTCATATTT
TAAACAGAGG ATATCGGCAT

1201 TTGTTTCTTT CTCTGAGGAC AAGAGAAAAA
AGCCAGGTTC CACAGAGGAC

1251 ACAGAGAAGG TTTGGGTGTC CTCCTGGGGT
TCTTTTTGCC AACTTTCCCC

1301 ACGTTAAAGG TGAACATTGG TTCTTTCATT
TGCTTTGGAA GTTTTAATCT

1351 CTAACAGTGG ACAAAGTTAC CAGTGCCTTA
AACTCTGTTA CACTTTTTGG

1401 AAGTGAAAAC TTTGTAGTAT GATAGGTTAT
TTTGATGTAA AGATGTTCTG

1451 GATACCATTA TATGTTCCCC CTGTTTCAGA
GGCTCAGATT GTAATATGTA

1501 AATGGTATGT CATTCGCTAC TATGATTTAA
TTTGAAATAT GGTCTTTTGG

1551 TTATGAATAC TTTGCAGCAC AGCTGAGAGA
GGCTGTCTGT TGTATTCATT

1601 GTGGTCATAG CACCTAACAA CATTGTAGCC
TCAATCGAGT GAGACAGACT

1651 AGAAGTTCCT AGTTGGCTTA TGATAGCAAA
TGGCCTCATG TCAAATATTA

1701 GATGTAATTT TGTGTAAGAA ATACAGACTG
GATGTACCAC CAACTACTAC

1751 CTGTAATGAC AGGCCTGTCC AACACATCTC
CCTTTTCCAT GCTGTGGTAG

1801 CCAGCATCGG AAAGAACGCT GATTTAAAGA
GGTGAGCTTG GGAATTTTAT

1851 TGACACAGTA CCATTTAATG GGGAGACAAA
AATGGGGGCC AGGGGAGGGA

1901 GAAGTTTCTG TCGTTAAAAA CGAGTTTGGA
AAGACTGGAC TCTAAATTCT

1951 GTTGATTAAA GATGAGCTTT GTCTACCTTC
AAAAGTTTGT TTGGCTTACC

2001 CCCTTCAGCC TCCAATTTTT TAAGTGAAAA
TATAACTAAT AACATGTGAA

2051 AAGAATAGAA GCTAAGGTTT AGATAAATAT
TGAGCAGATC TATAGGAAGA

2101 TTGAACCTGA ATATTGCCAT TATGCTTGAC
ATGGTTTCCA AAAAATGGTA

2151 CTCCACATAG TTCAGTGAGG GTAAGTATTT
TCCTGTTGTC AAGAATAGCA

2201 TTGTAAAAGC ATTTTGTAAT AATAAAGAAT
AGCTTTAATG ATATGCTTGT

2251 AACTAAAATA ATTTTGTAAT GTATCAAATA
CATTTAAAAC ATTAAAATAT

2301 AATCTCTATA AT (SEQ ID NO:15)

The wild type connexin 26 gene is published in D. T. Kiang et al. (1997) Gene 199 (1–2): 165–171.

TABLE 1

Mutations in the Cx26 coding exon in individuals affected with familial forms of prelingual deafness

| Family (geographical origin) | 30delG mutation | Other mutation | Deafness |
| --- | --- | --- | --- |
| DFNB1-linked families | | | |
| S15 (sTu) | homozygous | — | profound |
| S19 (sTu) | homozygous | — | profound |
| ST (sTu) | — | homozygous E47X | profound |
| 20 (nTu) | homozygous | — | profound |
| 60 (nTu) | homozygous | — | profound |
| LH (Leb) | homozygous | — | severe–profound |
| Families consistent with DFNB1 linkage | | | |
| 51 (NZ) | homozygous | — | severe–profound |
| 1160 (NZ) | homozygous | — | moderate–severe* |
| 1548 (NZ) | — | — | profound |
| 1608 (NZ) | homozygous | — | profound** |
| 1773 (NZ) | heterozygous | — | profound |
| 1873 individual II.3 (NZ) | homozygous | — | moderate |
| 1873 individual II.2 (NZ) | — | heterozyous 30del38 | profound |
| 1877 (NZ) | homozygous | — | profound |
| 9670 (Aust) | — | delE118/ R148P | moderate–severe |
| Families uncharacterized for DFNB1 linkage | | | |
| P1 (Fr) | homozygous | — | severe–profound |
| P2 (Fr) | — | — | profound |
| P3 (Leb) | homozygous | — | severe–profound |
| P4 (Tur) | — | — | severe–profound |
| P5 (Fr) | homozygous | — | profound |
| P6 (Fr) | heterozygous | — | severe–profound |
| P7 (Fr) | — | — | moderate |
| P8 (Fr) | — | — | moderate |
| L13131 (Fr) | — | — | profound |
| L14190 (Fr) | — | — | mild–moderate |
| P9 (Por) | homozygous | — | severe–profound |
| P10 (Fr) | homozygous | — | severe–profound |
| P11 (Fr) | heterozygous | — | moderate–severe |
| P12 (Fr) | — | — | severe–profound |
| P13 (Fr) | — | — | profound |
| P14 (Alg) | heterozygous | — | moderate–severe |
| P15 (Fr) | — | — | severe–profound |
| P16 (mother/Fr, father/Pol) | homozygous | — | severe** |
| P17 (Fr) | heterozygous | — | severe*** |
| 1885 (NZ) | heterozygous | — | profound |
| 2254 (NZ) | — | — | moderate–severe |

*moderate in one ear, severe in the other ear.
**moderate hearing loss in mother (severe at high frequencies),
***mild hearing loss in father, who are heterozygous carriers for the 30delG mutation.

The analysis reported here concerns deaf children of the various families except for family 1873 (see patients and methods).

* moderate in one ear, severe in the other ear.

moderate hearing loss in mother (severe at high frequencies), *mild hearing loss in father, who are heterozygous carriers for the 30delG mutation.

Geographical origins: (Alg) Algeria, (Aust) Australia, (Fr) 10 France, (Leb) Lebanon, (NZ) New Zealand, (Pol) Poland, (Por) Portugal, (nTu) North Tunisia, (sTu) South Tunisia, (Tur) Turkey

What is claimed is:

1. A purified polynucleotide comprising a nucleotide sequence containing a mutation of a wild-type connexin 26 gene, wherein the mutation comprises a deletion of a nucleotide from nucleotide 30 to nucleotide 32.

2. A purified polynucleotide, which hybridizes under stringent conditions specifically with a polynucleotide according to claim 1 and not with a wild-type connexin 26 gene.

3. An oligonucleotide useful as a primer or as a probe consisting of 15 to 50 consecutive nucleotides of the polynucleotide of claim 2, wherein the oligonucleotide specifically hybridizes under stringent conditions with a region of a mutated connexin 26 gene and not with a wild-type connexin 26 gene, wherein said region of said mutated connexin 26 gene comprises a deletion of a nucleotide from nucleotide 30 to nucleotide 32 of said wild-type connexin 26 gene.

4. A method for detecting the presence of a nucleotide deletion in the connexin 26 gene in a biological sample containing DNA, wherein the mutation comprises a deletion of a nucleotide from nucleotide 30 to nucleotide 32 comprising:
   a) bringing the biological sample into contact with an oligonucleotide primer according to claim 3, under conditions permitting a hybridization of the primer with the DNA contained in the biological sample;
   b) amplifying the DNA;
   c) detecting the amplification products; and
   d) detecting the mutation by appropriate techniques.

5. The method of claim 4, wherein in step d) the mutation is detected by one of the following techniques:
   single-strand conformation -polymorphism (SSCP); or
   denaturing gradient gel electrophores s (DGG:); or
   sequencing or
   temperature gradient gel electrophoresis (TGGE).

6. A method for detecting the presence of a nucleotide deletion in the connexin 26 gene in a biological sample containing DNA, wherein the mutation comprises a deletion of a nucleotide from nucleotide 30 to nucleotide 32 comprising:
   a) bringing the biological sample into contact with an oligonucleotide probe according to claim 3, under conditions permitting hybridization of the probe with the DNA contained in the biological sample; and
   b) detecting a hybrid formed between the oligonucleotide probe and the DNA contained in the biological sample.

7. The method according to claim 4, wherein before step a), the DNA contained in the biological sample is amplified using a pair of primers.

8. The method of claim 4, wherein step d) further comprises the steps of:
   a) incubating the amplification products with a labeled detection probe that hybridizes with both a normal connexin 26 sequence and a 30delG mutant sequence and a first capture probe that hybridize with said normal connexin 26 sequence but does not hybridize with said 30delG mutant sequence;
   b) incubating the amplification products with said labeled detection probe and a second capture probe that hybridizes with said mutant 30delG sequence but does not hybridize with said normal connexin 26 sequence;
   c) hybridizing the amplification products with said detection probe and with said first or second capture probe; and
   d) comparing the hybridization signal obtained from said first capture probe with the hybridization signal obtained from said second capture probe.

9. The method of claim 8, wherein said detection probe is non-radioactively labeled.

10. The method of claim 9, wherein said detection probe is labeled with biotin.

11. The method of claim 8, wherein said first and second capture probes are bound to a microplate.

12. A kit for detecting the presence of a nucleotide deletion in the connexin 26 gene in a biological sample, wherein the mutation comprises a deletion of a nucleotide from nucleotide 30 to nucleotide 32, said kit comprising:

a) an oligonucleotide as claimed in claim 3;
b) reagents for carrying out DNA amplification; and
c) a component for determining the length of the amplified fragments or for detecting a mutation.

* * * * *

UNITED STATES PATENT AND TRADEMARK OFFICE
CERTIFICATE OF CORRECTION

PATENT NO. : 6,485,908 B1
DATED : November 26, 2002
INVENTOR(S) : Christine Petit et al.

It is certified that error appears in the above-identified patent and that said Letters Patent is hereby corrected as shown below:

Title page,
Item [57], ABSTRACT,
Line 2, after "in" insert -- a --.
Line 4, "the mutated" should read -- said mutated --.

Column 23,
Line 61, "-polymorphism" should read -- polymorphism --.
Line 62, "electrophores s (DGG:)" should read -- electrophoresis (DGGE) --.

Column 24,
Line 49, "that hybridize" should read -- that hybridizes --.

Signed and Sealed this

Fifteenth Day of April, 2003

JAMES E. ROGAN
*Director of the United States Patent and Trademark Office*

SEQUENCE LISTING

<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
tcttttccag agcaaaccgc c                                         21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
tgagcacggg ttgcctcatc                                           20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
gacacgaaga tcagctgcag                                           20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
ccaggctgca agaacgtgtg                                           20

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
agacgatcct gggggtgtga acaaa                                     25

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6

```
atcctggggg tgtga                                                    15
```

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7

```
agacgatcct gggggctcac cgtcctc                                       27
```

<210> SEQ ID NO 8
<211> LENGTH: 2314
<212> TYPE: DNA
<213> ORGANISM: Homo sapiens

<400> SEQUENCE: 8

```
gatttaatcc tatgacaaac taagttggtt ctgtcttcac ctgttttggt gaggttgtgt     60
aagagttggt gtttgctcag gaagagattt aagcatgctt gcttacccag actcagagaa    120
gtctccctgt tctgtcctag ctagtgattc ctgtgttgtg tgcattcgtc ttttccagag    180
caaaccgccc agagtagaag atggattggg gcacgctgca gacgatcctg ggggtgtga    240
acaaacactc caccagcatt ggaaagatct ggctcaccgt cctcttcatt tttcgcatta    300
tgatcctcgt tgtggctgca aaggaggtgt ggggagatga gcaggccgac tttgtctgca    360
acaccctgca gccaggctgc aagaacgtgt gctacgatca ctacttcccc atctcccaca    420
tccggctatg ggccctgcag ctgatcttcg tgtccacgcc agcgctccta gtggccatgc    480
acgtggccta ccggagacat gagaagaaga ggaagttcat caaggggag ataaagagtg     540
aatttaagga catcgaggag atcaaaaccc agaaggtccg catcgaaggc tccctgtggt    600
ggacctacac aagcagcatc ttcttccggg tcatcttcga agccgccttc atgtacgtct    660
tctatgtcat gtacgacggc ttctccatgc agcggctggt gaagtgcaac gcctggcctt    720
gtcccaacac tgtggactgc tttgtgtccc ggcccacgga aagactgtc tttcacagtg     780
ttcatgattg cagtgtctgg aatttgcatc ctgctgaatg tcactgaatt gtgttatttg    840
ctaattagat attgttctgg gaagtcaaaa agccagtttt aacgcattgc ccagttgtta    900
gattaagaaa tagacagcat gagagggatg aggcaacccg tgctcagctg tcaaggctca    960
gtcgccagca tttcccaaca caaagattct gaccttaaat gcaaccattt gaaacccctg   1020
taggcctcag gtgaaactcc agatgccaca atgagctctg ctcccctaaa gcctcaaaac   1080
aaaggcctaa ttctatgcct gtcttaattt tctttcactt aagttagttc cactgagacc   1140
ccaggctgtt aggggttatt ggtgtaaggt actttcatat tttaaacaga ggatatcggc   1200
atttgtttct ttctctgagg acaagagaaa aaagccaggt tccacagagg acacagagaa   1260
ggtttgggtg tcctcctggg gttctttttg ccaactttcc ccacgttaaa ggtgaacatt   1320
ggttctttca tttgctttgg aagttttaat ctctaacagt ggacaaagtt accagtgcct   1380
taaactctgt tacacttttt ggaagtgaaa actttgtagt atgataggtt attttgatgt   1440
aaagatgttc tggataccat tatatgttcc ccctgtttca gaggctcaga ttgtaatatg   1500
taaatggtat gtcattcgct actatgattt aatttgaaat atggtctttt ggttatgaat   1560
actttgcagc acagctgaga gaggctgtct gttgtattca ttgtggtcat agcacctaac   1620
aacattgtag cctcaatcga gtgagacaga ctagaagttc ctagttggct tatgatagca   1680
```

```
aatggcctca tgtcaaatat tagatgtaat tttgtgtaag aaatacagac tggatgtacc      1740
accaactact acctgtaatg acaggcctgt ccaacacatc tccctttttcc atgctgtggt     1800 agccagcatc ggaaagaacg ctgatttaaa gaggtgagct tgggaatttt attgacacag      1860
taccatttaa tggggagaca aaaatggggg ccaggggagg gagaagtttc tgtcgttaaa      1920
aacgagtttg gaaagactgg actctaaatt ctgttgatta aagatgagct ttgtctacct      1980
tcaaaagttt gtttggctta ccccccttcag cctccaattt tttaagtgaa aatataacta    2040
ataacatgtg aaaagaatag aagctaaggt ttagataaat attgagcaga tctataggaa      2100
gattgaacct gaatattgcc attatgcttg acatggtttc caaaaaatgg tactccacat      2160
acttcagtga gggtaagtat tttcctgttg tcaagaatag cattgtaaaa gcattttgta      2220
ataataaaga atagctttaa tgatatgctt gtaactaaaa taattttgta atgtatcaaa      2280
tacatttaaa acattaaaat ataatctcta taat                                  2314

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
ctagtgattc ctgtgttgtg tgc                                               23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 10
ataatgcgaa aaatgaagag ga                                                22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11
aaaaaaaatc ctgggggggtg tg                                               22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
aaaaaaaatc ctgggggtgt ga                                                22

<210> SEQ ID NO 13
<211> LENGTH: 23
<212> TYPE: DNA
```

```
<213> ORGANISM: Artificial Sequence
<220> FEATURE:
<223> OTHER INFORMATION: Description of Artificial Sequence:
      Oligonucleotide

<400> SEQUENCE: 13
cagcattgga aagatctggc tca                                             23

<210> SEQ ID NO 14
<211> LENGTH: 63
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
cgcccgccgc gccccgcgcc cggcccgccg ccccccgcccc ctagtgattc ctgtgttgtg    60
tgc                                                                   63

<210> SEQ ID NO 15
<211> LENGTH: 2312
<212> TYPE: DNA
<213> ORGANISM: Homo sapiens

<400> SEQUENCE: 15
gatttaatcc tatgacaaac taagttggtt ctgtcttcac ctgttttggt gaggttgtgt    60
aagagttggt gtttgctcag gaagagattt aagcatgctt gcttacccag actcagagaa   120
gtctccctgt tctgtcctag ctatgttcct gtgttgtgtg cattcgtctt ttccagagca   180
aaccgcccag agtagaagat ggattggggc acgctgcaga cgatcctggg gggtgtgaac   240
aaacactcca ccagcattgg aaagatctgg ctcaccgtcc tcttcatttt tcgcattatg   300
atcctcgttg tggctgcaaa ggaggtgtgg ggagatgagc aggccgactt tgtctgcaac   360
accctgcagc caggctgcaa gaacgtgtgc tacgatcact acttccccat ctcccacatc   420
cggctatggg ccctgcagct gatcttcgtg tccagcccag cgctcctagt ggccatgcac   480
gtggcctacc ggagacatga agaagaggag aagttcatca agggggagat aaagagtgaa   540
tttaaggaca tcgaggagat caaaacccag aaggtccgca tcgaaggctc cctgtggtgg   600
acctacacaa gcagcatctt cttccgggtc atcttcgaag ccgccttcat gtacgtcttc   660
tatgtcatgt acgacggctt ctccatgcag cggctggtga agtgcaacgc ctggcccttgt  720 cccaacactg tggactgctt tgtgtcccgg cccacggaga agactgtctt tcacagtgtt   780
catgattgca gtgtctggaa tttgcatcct gctgaatgtc actgaattgt gttatttgct   840
aattagatat tgttctggga agtcaaaaaa gccagtttaa cgcattgccc agttgttaga   900
ttaagaaata gacagcatga gagggatgag gcaacccgtg ctcagctgtc aaggctcagt   960
cgccagcatt tcccaacaca agattctgac cttaaatgca accatttga aaccccctgta  1020 ggcctcaggt gaaactccag atgccacaat gagctctgct cccctaaagc tcaaaaacaa  1080
aggcctaatt ctatgcctgt cttaattttc tttcacttaa gttagttcca ctgagacccc  1140
aggctgttag gggttattgg tgtaaggtac tttcatattt taaacagagg atatcggcat  1200
ttgtttcttt ctctgaggac aagagaaaaa agccaggttc cacagaggac acagagaagg  1260
tttgggtgtc ctcctgggt tcttttttgcc aactttcccc acgttaaagg tgaacattgg  1320
ttctttcatt tgctttggaa gttttaatct ctaacagtga caaagttac cagtgcctta  1380 aactctgtta cacttttttgg aagtgaaaac tttgtagtat gataggttat tttgatgtaa  1440
```

```
-continued agatgttctg gataccatta tatgttcccc ctgtttcaga ggctcagatt gtaatatgta   1500
aatggtatgt cattcgctac tatgatttaa tttgaaatat ggtcttttgg ttatgaatac   1560
tttgcagcac agctgagaga ggctgtctgt tgtattcatt gtggtcatag cacctaacaa   1620
cattgtagcc tcaatcgagt gagacagact agaagttcct agttggctta tgatagcaaa   1680
tggcctcatg tcaaatatta gatgtaattt tgtgtaagaa atacagactg gatgtaccac   1740
caactactac ctgtaatgac aggcctgtcc aacacatctc cctttccat gctgtggtag    1800 ccagcatcgg aaagaacgct gatttaaaga ggtgagcttg ggaattttat tgacacagta   1860
ccatttaatg gggagacaaa aatggggggcc aggggaggga gaagtttctg tcgttaaaaa  1920
cgagtttgga aagactggac tctaaattct gttgattaaa gatgagcttt gtctaccttc   1980
aaaagtttgt ttggcttacc cccttcagcc tccaattttt taagtgaaaa tataactaat   2040
aacatgtgaa aagaatagaa gctaaggttt agataaaatat tgagcagatc tataggaaga  2100
ttgaacctga atattgccat tatgcttgac atggtttcca aaaaatggta ctccacatag   2160
ttcagtgagg gtaagtattt tcctgttgtc aagaatagca ttgtaaaagc attttgtaat   2220
aataaagaat agctttaatg atatgcttgt aactaaaata attttgtaat gtatcaaata   2280
catttaaaac attaaaatat aatctctata at                                 2312
```